United States Patent
Vecer et al.

(10) Patent No.: US 6,721,050 B2
(45) Date of Patent: Apr. 13, 2004

(54) METHOD AND DEVICE FOR THE SPECTRAL ANALYSIS OF LIGHT

(75) Inventors: Jaroslav Vecer, Praha (CZ); Petr Herman, Baltimore, MD (US)

(73) Assignee: Microcosm Inc., Columbia, MD (US)

( * ) Notice: Subject to any disclaimer, the term of this patent is extended or adjusted under 35 U.S.C. 154(b) by 341 days.

(21) Appl. No.: 09/801,838

(22) Filed: Mar. 8, 2001

(65) Prior Publication Data

US 2001/0024276 A1 Sep. 27, 2001

(30) Foreign Application Priority Data

Mar. 20, 2000 (CZ) ......................................... 2000-1015

(51) Int. Cl.$^7$ ................................................ G01J 4/00
(52) U.S. Cl. ...................................... 356/364; 356/368
(58) Field of Search ................................ 356/364, 368, 356/370

(56) References Cited

U.S. PATENT DOCUMENTS 5,949,480 A * 9/1999 Gerhart et al. .............. 356/368
6,373,569 B1 * 4/2002 Herman et al. ............. 356/364

* cited by examiner

*Primary Examiner*—Michael P. Stafira
*Assistant Examiner*—Juan D Valentin, II
(74) *Attorney, Agent, or Firm*—William S. Ramsey

(57) ABSTRACT

The method uses a physical phenomenon of dispersion of the optical rotation for identification of the spectral characteristics of light Polychromatic linearly polarized radiation passes through the environment that rotates a polarization plane of its spectral components, depending on their wavelength. After a subsequent passage through the analyzing polarizer, a dependence of the light intensity $S(\phi)$ on the angle $\phi$, that the analyzing polarizer forms with the polarization plane of the analyzed light, is measured. $S(\phi)$ is in a mathematical relationship with the spectrum of the analyzed radiation $I(\lambda)$, where $\lambda$ is a wavelength. $S(\phi)$ allows for the determination of the spectral characteristics of the analyzed radiation. In devices based on the above principle, the collimated polarized beam of the analyzed radiation passes first through the optical element that exhibits a dispersion of the optical rotation, i.e. rotator (4), then through the analyzing polarizer (5), and after a projection is detected by a proper detector (7). The detector measures $S(\phi)$ as a function of the angle $\phi$ of the analyzer. From $S(\phi)$ the parameters of the spectrum $I(\lambda)$ are determined.

4 Claims, 2 Drawing Sheets

METHOD AND DEVICE FOR THE SPECTRAL ANALYSIS OF LIGHT

This application claims priority under 35 U.S.C. 119(a)–(d) based on Czech Republic Patent Application PV2000-1015 filed Mar. 20, 2000.

TECHNICAL FIELD

The invention pertains to the spectral analysis of light.

BACKGROUND OF INVENTION

The currently used procedures for the spectral analysis of light can be divided into three groups. The first and oldest approach is based on the angular spectral separation of light. The light, upon interaction with a suitable optical element (optical prism, optical grating), changes the direction of propagation. This direction depends on the wavelength. Such spectrally separated components can be independently analyzed. The second, frequently used procedure is based on the phenomenon of light interference when a spectrum of the analyzed radiation can be calculated from the interferogram. The third, recently published procedure uses the phenomenon of the dispersion of the optical rotation (CZ Patent 284 282). When the linearly polarized light passes through a proper element (rotator), its polarization plane rotates as a function of wavelength. This can be used for measurement of its spectrum.

DETAILED DESCRIPTION

The subject of the invention is a new method for measurement of spectral characteristics of light originating at a distant point light source, object or at two dimensional scene. The method is based on the phenomenon of dispersion of the optical rotation. The invention is a modification of the method patented in CZ 284 282. The principle of the method is illustrated in FIG. 1. The analyzed beam of radiation 2 emerging from the aperture 1 is converted by passing through optical system 3 and polarizer 5 to a linearly polarized parallel beam of radiation 6. This collimated polarized radiation is subjected to the optical rotation in the environment with a dispersion of the optical rotation (rotator) 7. The extent of this rotation is selected according to the spectral interval in which the spectral analysis is being done. It means that the optical rotation of the rotator can be with an advantage adjusted differently for broad-band and for narrow-band radiation, as well as for radiation from different spectral regions, i.g. for uv, vis or ir radiation. The rotator outputs radiation 8 having polarization planes of the individual spectral components rotated. The extent of the rotation depends on the wavelength of the spectral component. Such parallel beam passes through the second polarizer 9 (analyzer). The polarization plane 17 of the analyzer forms an angle $\phi=\phi_1$ with the polarization plane of the analyzed radiation 16. The beam 10 is focused by the optical system 11 on the detector 13. Then, the intensity S of the output beam 10 is measured by a single or a multichannel detector. The procedure is repeated with fixed parameters of the rotator for a set of angles $\phi$ from the interval $(\phi_1,\phi_2)$. Such procedure yields functional dependence of the output intensity $S(\phi)$ on the angle $\phi$. Spectral characteristics of the analyzed radiation are then extracted from this dependence by a mathematical analysis. The spectral characteristics obtained can be either a full spectrum, or some characteristic spectral parameter only, for example a location of the spectral maximum, a spectral half-width, etc.

When spectral characteristics of a point light source are measured, the collimated polarized radiation 6 passes through the optically active environment 7 that exhibits the same dispersion of the optical rotation in the entire crossection of the analyzed beam. The output light beam 8 is then directed on a single-channel detector which measures the light intensity $S(\phi)$.

When spectral characteristics of a planar light source 18, FIG. 2, or of a distant scene are measured, the collimated polarized radiation 6 passes through the optically active environment 7 that exhibits the same dispersion of the optical rotation in the entire crossection of the beam and the output intensity 8 of the light is focused by the optical system 11 on a multi-channel detector 20. Each pixel of the detector measures intensity of a corresponding point in the field of view. This process is known as imaging.

The device according to the presented method consists of a collimating optical system 3 and a detector 13, FIG. 1. Importantly, the first polarizer 5, rotator 7, and the second polarizer 9 are placed between the optical system 3 and the detector 13. The rotator must exhibit a non-zero dispersion of the optical rotation and its parameters affecting the amount of the optical rotation experienced by the light do not change during the measurement. When collimated or polarized radiation is analyzed, the device does not require the collimating optical system 3 or the first polarizer 5, respectively.

An advantage of the method for the spectral analysis of light and an advantage of the device using the new method is that, in comparison with the previously published method, the parameters of the rotator do not change during the measurement. Only the second polarizer 9 rotates instead.

For the identification of spectral characteristics of the input radiation according to the new method, the output intensity is measured for a set of different angles $\phi$ of the analyzing polarizer. For collimated, polarized, polychromatic beam of light 6 with wavelengths from the spectral interval $(\lambda_1,\lambda_2)$, the intensity $S(\phi)$, after passing through the rotator 7 and through the analyzer 9, is measured as a function of the angle $\phi$ from the interval $(\phi_1,\phi_2)$:

$$S(\varphi) = \int_{\lambda_1}^{\lambda_2} I(\lambda)\cos^2[\theta(\lambda)-\varphi]d\lambda \tag{1}$$

where $I(\lambda)$ is a spectrum of the input radiation, $\phi$ is an angle 16 between the polarization plane of the analyzer and a polarization plane of the linearly polarized input light, and $\theta(\lambda)$ is a rotation angle 15 of the polarization for the radiation with wavelength $\lambda$ after a passage through the rotator. The function $\theta(\lambda)$ is known for a given rotator and depends on geometric and material properties of the rotator. Since the function $S(\phi)$ has a period $\pi$, measurements for angles $\phi_2-\phi_1>\pi$ do not provide any new information and do not need to be done. Characteristics of the spectrum $I(\lambda)$ are determined from the dependence of $S(\phi)$ on $\phi$ described by Eq. (1). Depending on the complexity of the function $I(\lambda)$, it can be either the full spectrum, or some of its spectral parameters, e.g. wavelength of the spectral maximum, spectral half-width, etc.

In the device that works according to the above presented principle, the linearly polarized parallel beam of radiation 6 first passes through the optical rotator 7 where the polarization planes of the individual spectral components of radiation rotate in dependence on their wavelengths, further passes through the analyzer 9, and then the radiation 12 impinges on the detector which measures intensity $S(\phi)$ as a function of the rotation angle $\phi$ of the analyzing polarizer 9. Characteristics of the spectrum $I(\lambda)$ are then determined from the formula for $S(\phi)$, Esq. (1).

BRIEF DESCRIPTION OF DRAWINGS

The principle of the method for the spectral analysis of the electromagnetic radiation and one of the acceptable devices for its utilization is shown in FIG. 1.

EXAMPLES

Example No. 1

Figure 2:
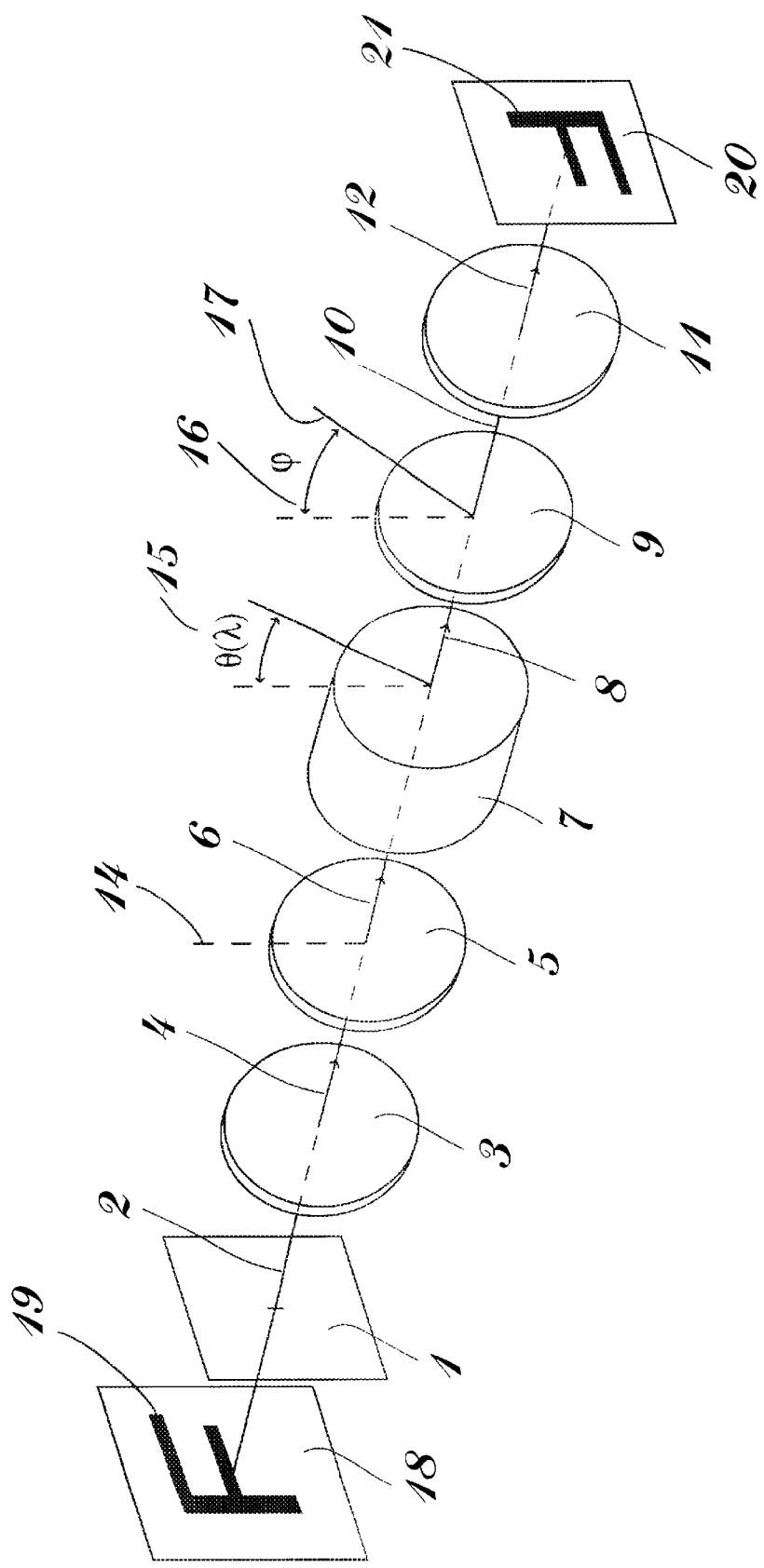
FIG. 2 demonstrates usage of the method for imaging applications.

A multi-channel measurement of the spectral characteristics of the planar light source or of a distant scene (spectral imaging), FIG. 2. The analyzed light 2 emerging from the input aperture 1 is collimated by the optical system 3, and linearly polarized by the polarizer 5. The light then passes through the rotator 7, analyzer 9, and it is projected by the optical system 11, onto the multichannel detector 20, which measures the function $S(\phi)$. Different elements 19 of the light source or of the scene are projected on corresponding pixels 21 of the multichannel detector 20. Then intensities $S(\phi)$ are simultaneously measured at all pixel locations. By repeating the measurement for a set angles $\phi$, 16, a stack of images $S(\phi)$ is collected. Then spectral map of the investigated object is obtained by the stack analysis. The spectrally mapped can be either the spectrum, or some of its parameters spectrally characterizing the analyzed source of light 18. The analysis could yield e.g. maps of a position of the spectral maximum, spectral half-width of similar parameters.

Example No. 2

The new method allows for a simple determination of wavelength of monochromatic radiation. For monochromatic radiation with the wavelength $\lambda_0$, there always exists a rotation angle $\phi=\phi_{\lambda 0}$ of the analyzer, for which the passing intensity equals to zero. As can be seen from Eq(1), intensity $S(\phi_0)$ equals to zero always when $\cos^2[\theta(\lambda_0)-\phi_{\lambda 0}]=0$, i.e. when equality $\theta(\lambda_0)-\phi_{\lambda 0}=(2k-1)\cdot\pi/2$ holds true. Symbol k represents a natural number. Since the rotator exhibits non-zero dispersion of the optical rotation, different wavelengths $\lambda_0$ require different adjustment of the analyzer angle $\phi_{\lambda 0}$ in order to fully extinct the output intensity $S(\phi)$. Therefore the angular scale of the analyzer can be absolutely calibrated in wavelengths. Since the extinction angle $\phi_{\lambda 0}$ can be found very accurately, the wavelength calibration is also very accurate. The method can be used e.g. for measurement and monitoring of wavelength of light generated by tunable lasers or by other narrow-band light sources.

The method consists of passing polarized monochromatic light 6 with the wavelength $\lambda_0$ through the rotator 7 and analyzer 9, adjusting the angle $\phi$, 16, of the analyzer to the value $\phi_{\lambda 0}$ when output intensity 10 extincts, and determination of the wavelength $\lambda_0$ by e.g. comparing the $\phi_{\lambda 0}$ value with the calibration curve.

Figure 1:
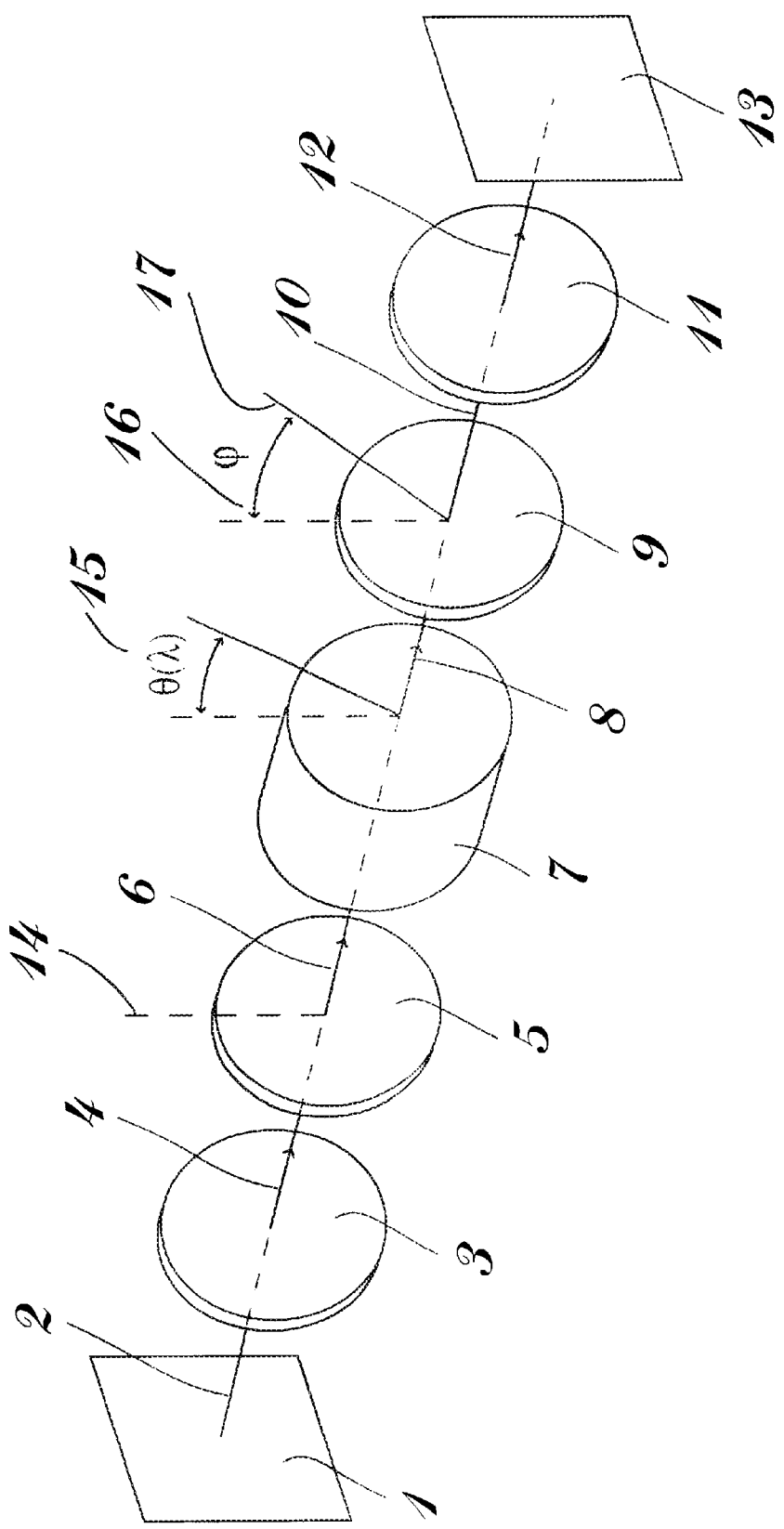

The device for the absolute spectral calibration of the monochromatic non-polarized collimated radiation consists, according to FIG. 1, of the polarizer 5, rotator 7, and analyzer 9. For polarized input radiation the polarizer 5 can be omitted. Correct adjustment of the angle $\phi=\phi_{\lambda 0}$ of the analyzer can be detected visually or electronically with the use of the detector 13. Optical systems 3 and 11 may be omitted when parallel beam of light, e.g. a beam emitted from laser, is analyzed.

Example No. 3

This disclosed method also allows for a simple determination of the spectral half-width of lights sources emitting band-shaped radiation centered at the wavelength $\lambda_0$. For such radiation 2, FIG. 1, it is not possible to find the angle $\phi=\phi_{\lambda_o}$ of the analyzer 9, for witch the passing intensity $S(\phi_{\lambda_o})$, 10, equals to zero. Instead, an analyzer angle $\phi=\phi_{min}$ can be found for which the passing light intensity is at its minimum, i.e. $S(\phi_{min})=S_{min}$. When the analyzer is turned by 90° from this position, i.e. for the analyzer angle $\phi_{max}=(\phi_{min}+\pi/2)$ or $\phi_{max}=(\phi_{min}-\pi/2)$, the passing intensity is as its maximum and intensity $S_{max}$ can be measured with the detector 13. Due to the non-zero dispersion of the optical rotation of the rotator 7, the ratio $W=S_{min}/S_{max}$ is directly related to the spectral half-width of the analyzed light. The value of W increases with increasing spectral half-width and it approaches zero for the monochromatic light. Different angles $\phi_{min}$ of the analyzer, for which the output intensity 10 is minimal, can be related to different central wavelengths $\lambda_0$. Both spectral half-width and $\lambda_0$ can be obtained e.g. by comparing the value of W and $\phi_{min}$, respectively, with a calibration curve.

The method consist of passing polarized broadband light 6 with the central wavelength $\lambda_0$ through the rotator 7 and analyzer 9, adjusting the angle $\phi$, 16, of the analyzer 9 to the value $\phi=\phi_{min}$ when output intensity S is minimal, measuring the minimal intensity $S_{min}$, turning the analyzer 9 by 90°, measuring the intensity $S_{max}$, calculating the ratio $W=S_{min}/S_{max}$, and determining of the spectral half-width and the wavelength $\phi_0$ e.g. from the calibration curves.

Without limiting the applicability, the method outlined in this example can be used for determination of the spectral half-width of the light generated by pulsed femtosecond lasers. Since the spectral half-width of the ultrashort light pulses is directly related to the duration of the pulse, this method also allows for measurements of the duration (time-width) of the light pulses.

The device for the measurement of the spectral half-width consists, according to FIG. 1, of the polarizer 5, rotator 7, and the analyzer 9. For polarized input radiation, the polarizer 5 can be omitted. Optical systems 3 and 11 may be omitted, when parallel beam of light, e.g. a beam emitted from a laser, is analyzed. Correct adjustment of the analyzer angles $\phi_{min}$ and $\phi_{max}$ can be detected visually or electronically with the use of the detector 13.

INDUSTRIAL APPLICATION

The invention can be used everywhere where it is necessary to analyze spectral composition of light. The invention is ideally suited for applications where it is necessary to generate a color-contrast with monochrome CCD cameras. The new method can also be used for accurate absolute measurement of the wavelength of a monochromatic radiation and for evaluation of the spectral half-width of the light sources with a band-shaped spectral profile. For the femtosecond lasers, it is possible to determine the pulse width from the spectral half-width.

What is claimed is:

1. A method for the measurement of the spectral characteristics of light comprising:
    converting the analyzed beam of radiation with a spectrum $I(\lambda)$ from the wavelengths interval $(\lambda_1,\lambda_2)$ to the linearly polarized parallel beam of radiation,
    subjecting this collimated polarized radiation to optical rotation in the optically active environment with dispersion of the optical rotation, whereby individual light waves rotate by amounts $\theta(\lambda)$ characteristic of their wavelengths $\lambda$,
    polarizing the newly formed parallel beam in the plane forming angle $\phi=\phi_1$ with the polarization plane of the linearly polarized analyzed radiation, measuring the output intensity of the analyzed beam by a detector, changing the angle ϕ, measuring the output intensity of the analyzed-radiation again, repeating the measuring and changing procedure for a set of angles ϕ from the interval ($ϕ_1$, $ϕ_2$), thereby obtaining the function dependence S(ϕ) of the output intensity of the analyzed radiation on the angle ϕ:

$$S(\varphi) = \int_{\lambda_1}^{\lambda_2} I(\lambda)\cos^2[\theta(\lambda) - \varphi]d\lambda,$$

and determining spectral characteristics of the analyzed light I(λ) from the measured dependence S(ϕ).

2. The method of claim 1, wherein the spectral characteristics of light are spectral characteristics of a point light source, the optically active environment exhibits the same dispersion of the optical rotation in the entire cross section of the analyzed beam, and the output intensity is measured with a single-channel detector.

3. The method of claim 1, wherein the spectral characteristics of light are spectral characteristics of the planar light source or the distant scene, the optically active environment exhibits the same dispersion of the optical rotation in the entire cross section of the analyzed beam, and the output intensity is measured with a multi-channel detector.

4. The method of claim 1, wherein the minimum and maximum of the output intensity of light is being measured, and the wavelength of the spectral maximum and the spectral half-width of the spectral band of the analyzed radiation is being determined from these values by comparison of their ratio with the experimental calibration, or with the calibration determined from the functional dependence of S(ϕ) in claim 1.

* * * * *